United States Patent
Tear et al.

(10) Patent No.: US 9,421,243 B2
(45) Date of Patent: Aug. 23, 2016

(54) THERAPY FOR INFLUENZA LIKE ILLNESS

(75) Inventors: Victoria Jane Tear, Southampton (GB); James Jonathan Welch Roberts, Southampton (GB); Phillip David Monk, Sway (GB)

(73) Assignee: SYNAIRGEN RESEARCH LIMITED (GB)

( * ) Notice: Subject to any disclaimer, the term of this patent is extended or adjusted under 35 U.S.C. 154(b) by 0 days.

(21) Appl. No.: 13/583,976

(22) PCT Filed: Mar. 10, 2011

(86) PCT No.: PCT/GB2011/050480
§ 371 (c)(1), (2), (4) Date: Nov. 26, 2012

(87) PCT Pub. No.: WO2011/110861
PCT Pub. Date: Sep. 15, 2011

(65) Prior Publication Data
US 2013/0064792 A1 Mar. 14, 2013

(30) Foreign Application Priority Data

Mar. 12, 2010 (GB) .................................. 1004144.0
May 17, 2010 (GB) .................................. 1008114.9

(51) Int. Cl.
*A61K 38/21* (2006.01)
*C07K 14/565* (2006.01)
*A61K 38/00* (2006.01)
*C07K 14/11* (2006.01)

(52) U.S. Cl.
CPC ............. *A61K 38/215* (2013.01); *C07K 14/565* (2013.01); *A61K 38/00* (2013.01); *A61K 2121/00* (2013.01); *C07K 14/11* (2013.01)

(58) Field of Classification Search
None
See application file for complete search history.

(56) References Cited

U.S. PATENT DOCUMENTS

| | | | |
|---|---|---|---|
| 6,030,609 | A | 2/2000 | Panuska et al. |
| 7,569,216 | B2 | 8/2009 | Davies et al. |
| 2006/0153803 | A1 | 7/2006 | Tan et al. |
| 2007/0134763 | A1* | 6/2007 | Davies et al. ................. 435/69.1 |
| 2008/0260690 | A1* | 10/2008 | De Luca ...................... 424/85.6 |
| 2008/0292559 | A1 | 11/2008 | Condos et al. |

FOREIGN PATENT DOCUMENTS

| | | |
|---|---|---|
| CA | 2 589 613 | 11/2008 |
| GB | 0405634.7 | 3/2004 |
| WO | 2004/108151 A1 | 12/2004 |
| WO | WO 2005/087253 A2 | 9/2005 |
| WO | WO 2006/082435 A1 | 8/2006 |
| WO | WO 2007/029041 A2 | 3/2007 |
| WO | WO 2007/057436 A2 | 5/2007 |
| WO | WO 2007/132271 A2 | 11/2007 |

OTHER PUBLICATIONS

CDC Overview of Influenza surveillance in the United States, Oct. 2014, pp. 1-5.*
Rhinovirus Infections (2006, American Academy of Pediatrics, p. 1-2.*
Thomson Reuters Drug News (formerly DailyDrugNews.com), Nov. 20, 2009, "Synairgen competes phase I safety trial of inhaled IFN-beta in asthma", XP002660104.
Synairgen plc Press Release, "New data for the treatment of 'severe' influenza lung infection", XP-002660105.
Hayman et al., "Variation in the ability of human influenza A viruses to induce and inhibit the IFN-β pathway", Virology 347 (2006), pp. 52-64.
Scott, "Interfering with the real cold", British Medical Journal, vol. 292, May 31, 1986.
Kugel et al., "Intranasal administration of alpha interferon reduces seasonal influenza A virus morbidity in ferrets", Journal of Virology, Apr. 2009, pp. 3843-3851.
Treanor et al., "Intranasally administered interferon as prophylaxis against experimentally induced influenza a virus infection in humans", The Journal of Infectious Disease, vol. 156, No. 2, Aug. 1987.
Kelley et al., "The causes and diagnoses of influenza-like illness", Theme—reprinted from Australian Family Physician vol. 33, No. 5, May 2004, pp. 305-309.
Szretter et al., "Early control of H5N1 influenza virus replication by the type I interferon response in mice", Journal of Virology, Jun. 2009, vol. 83, No. 11, pp. 5825-5834.
Wiselka et al., "Prophylactic intranasal $\alpha_2$ interferon and viral exacerbations of chronic respiratory disease", Thorax, 1991, vol. 46, pp. 706-711.
Cheng et al. "Performance of laboratory diagnostics for the detection of influenza A(H1N1)v virus as correlated with the time after symptom onset and viral load", Journal of Clinical Virology, 47, (2010), pp. 182-185.
Baccam et al., "Kinetics of influenza A virus infection in humans"; Journal of Virology, Aug. 2006, vol. 80, No. 15, pp. 7590-7599.
Phillpotts et al., "Intranasal lymphoblastoid interferon ("Wellferon") prophylaxis against rhinovirus an influenza virus in volunteers", Journal of Interferon Research 1984, 4, pp. 535-541.
Lee et al., "Viral loads and duration of viral shedding in adult patients hospitalized with influenza", Chicago Journals—The Journal of Infectious Diseases, Aug. 15, 2009, vol. 200, No. 4.
Kuiken et al., "Pathology of human influenza revisited", Vaccine, 265 (2008), pp. D59-D66.
Van Hoeven et al., "Pathogenesis of 1918 pandemic and H5N1 influenza virus infections in a guinea pig model: antiviral potential of exogenous alpha interferon to reduce virus shedding", Journal of virology, Apr. 2009, vol. 83, No. 7, pp. 2851-2861.

(Continued)

*Primary Examiner* — Christine J Saoud
*Assistant Examiner* — Jegatheesan Seharaseyon
(74) *Attorney, Agent, or Firm* — Wood, Phillips, Katz, Clark & Mortimer

(57) ABSTRACT

An agent selected from: (a) interferon-β (IFN-β); (b) an agent that increases IFN-β expression; or (c) a polynucleotide which is capable of expressing (a) or (b); for use in the treatment of individuals with lower respiratory tract illness that has developed during or following an established ILI, wherein said treatment is by airway delivery of said medicament.

5 Claims, 6 Drawing Sheets

(56) References Cited

OTHER PUBLICATIONS

Thompson et al., "Influenza-associated hospitalizations in the United States", JAMA, Feb. 24, 2010, (reprinted Sep. 15, 2004, vol. 292, No. 11, pp. 1333-1340).

International Preliminary Report on Patentability issued Sep. 18, 2012 in corresponding International Application No. PCT/GB2011/050480.

Encyclopedia Britannica Concise; Common cold—Encyclopedia Article and More from Merriam-Webster; printed Nov. 12, 2014, pp. 1-2.

Anonymous: "Influenza-like illness—Wikipedia, the free encyclopedia", Feb. 16, 2010, XP055195853.

Examination Report for corresponding application No. EP 11 730 046.7 dated Jul. 2, 2015.

* cited by examiner

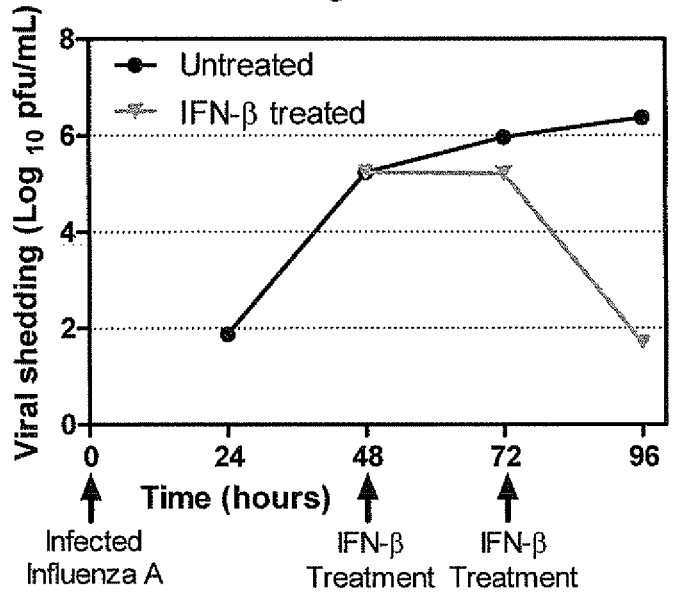
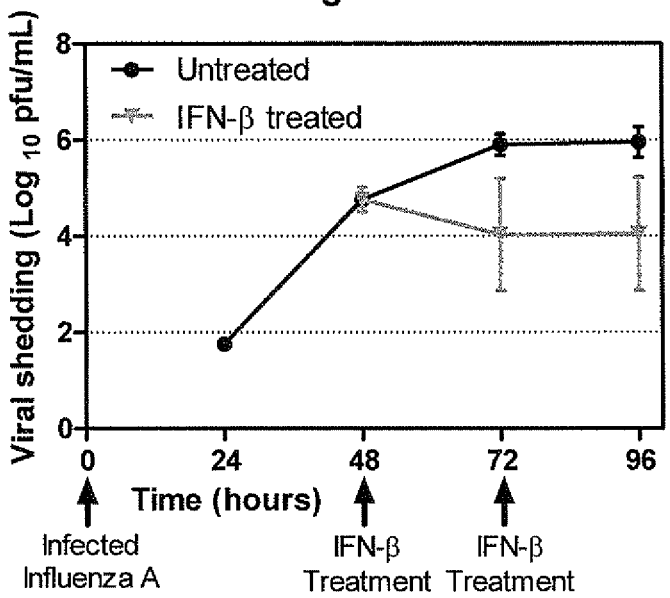

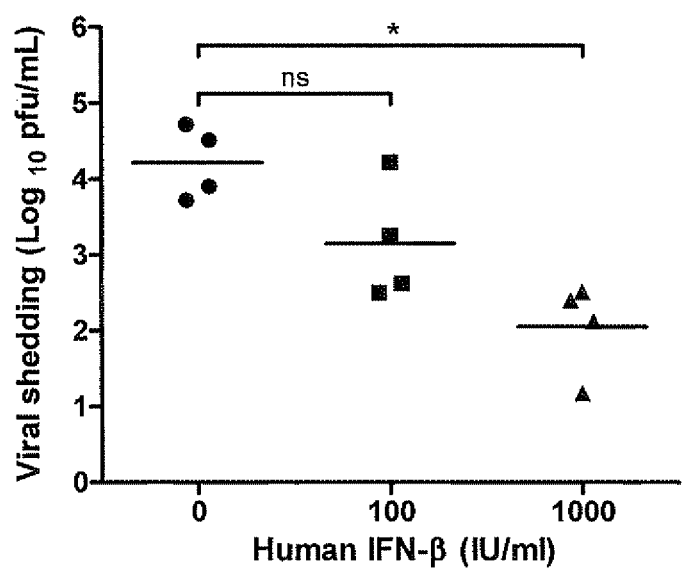

Synairgen Interferon Beta Proof of Successful Delivery Study

| | | | | | administration | | administration | |
|---|---|---|---|---|---|---|---|---|
| Group | No/Group | Treatment | | Day -7 | Day 0 | Day 1 (24 hrs) | Day 8 | Day 9 (24 hrs) |
| 1 | 5 | Interferon Beta | | B, W, BAL | B, W, Aerosol delivery of Interferon Beta Dose 1 | B, W, BAL | B, W, Aerosol delivery of Interferon Beta Dose 2 | B, W, BAL |
| HOUSING | | | | Standard (group) | | | | |

*BAL = broncheo alveolar lavage; W = body weight; B = Whole blood for serum

Figure 6

Synairgen Interferon Beta H5N1/H1N1 Treatment, Challenge & Sampling Schedule

| Group | No/Group | Treatment | d-14 | d -1 | | d 0 | +4 hrs | d1 | d2 | d3 | d4 | d5 |
|---|---|---|---|---|---|---|---|---|---|---|---|---|
| 1 | 9 | Vehicle | | | placebo | | n/a | | | | | |
| 2 | 9 | Interferon Beta Prophylaxis | B, TS | S, W, B | INFβ | Intratracheal CHALLENGE Influenza virus A/Indonesia/5/05 (H5N1) or A/Netherlands/602/2009 (H1N1) | n/a | S,B | S,B | S,B | S,B | Euthanasia S, W, LT, B |
| 3 | 9 | Interferon Beta Therapy | | | n/a | | INFβ | | | | | |
| HOUSING | | | Standard (group) | ISOLATOR | | | | | | | | |

* B = Whole blood for serum; S = throat & nose swabs; LT = lung tissue after sacrification; TS = temp sensor implantation; W = body weight

Figure 7

THERAPY FOR INFLUENZA LIKE ILLNESS

This application is a national stage application, filed under 35 U.S.C. 0371, of PCT/GB2011/050480, filed Mar. 10, 2011, which relies on GB 1004144.0, filed Mar. 12, 2010, and GB 1008114.9, filed May, 17, 2010, for priority, the disclosures of which are herein incorporated by reference in their entirety.

FIELD OF THE INVENTION

The invention relates to the treatment of individuals with lower respiratory tract illness that has developed during or following an established influenza-like illness (ILI). By established influenza like illness, we mean an illness in which the symptoms have been apparent, e.g., to the individual or to a carer, for at least 24 hours, more particularly at least 48 hours. More specifically, the invention relates to the treatment of individuals with lower respiratory tract illness that have developed during or following an ILI, particularly hospitalized patients, by delivery of interferon-β (IFN-β) or an agent that increases IFN-β expression by aerosol to the lower respiratory tract. Influenza like illness is a disease characterised by two of the following symptoms: headache, cough, sore throat, and myalgia and/or confirmed influenza. More specifically, ILI may be defined as a fever >37.8° C. plus two of the following symptoms: (headache, cough, sore throat, and myalgia) and/or confirmed influenza infection.

BACKGROUND OF THE INVENTION

Seasonal influenza is a common infection, especially during winter. Every year strains of influenza (type A or B) circulate, giving rise to clinical consultations in primary care, episodes of hospital treatment (mainly in older persons and young children, but occasionally in middle aged adults), and deaths (mainly in the elderly). Treatment in primary care and hospital may be required due to the direct effects of influenza virus infection or its possible complications, most commonly secondary bacterial infection. Increases in primary care consultations for ILI and winter bed pressures are frequently associated with periods of known community influenza activity.

Pandemic influenza occurs when a new influenza virus subtype emerges which is markedly different from recently circulating subtypes and strains, and is able to:
  infect humans;
  spread efficiently from person to person;
  cause significant clinical illness in a high proportion of those infected.

Because the virus is novel in humans, a high proportion of the population will have little or no immunity, producing a large pool of susceptible persons; accordingly the disease spreads widely and rapidly.

Interferons have previously been proposed for either prophylactic or early stage intervention in the treatment of influenza, but with limited success.

Highly pathogenic influenza is a virulent form of influenza, such as H5N1, which leads to a rapid and high level of morbidity.

ILI includes seasonal influenza, pandemic influenza and highly pathogenic influenza.

We have now found a new method of treating individuals, particularly hospitalized patients, with lower respiratory tract illness that has developed during or following an ILI.

SUMMARY OF THE INVENTION

Accordingly, the invention provides an agent selected from:
 (a) interferon-β (IFN-β);
 (b) an agent that increases IFN-β expression; or
 (c) a polynucleotide which is capable of expressing (a) or (b);
for use in the treatment of individuals with lower respiratory tract illness that have developed during or following an established ILI, wherein said treatment is by aerosol delivery to the lower respiratory tract of said agent.

The invention further provides a method of treating an individual diagnosed with lower respiratory tract illness that has developed during or following an established ILI comprising aerosol delivery to the lower respiratory tract of the individual of an agent selected from the group consisting of:
 (a) interferon-β (IFN-β);
 (b) an agent that increases IFN-β expression;
 (c) a polynucleotide which is capable of expressing (a) or (b).

Also provided is the use of an agent selected from:
 (a) interferon-β (IFN-β);
 (b) an agent that increases IFN-β expression; or
 (c) a polynucleotide which is capable of expressing (a) or (b);
In the preparation of a medicament for the treatment of lower respiratory tract illness that has developed during or following an established ILI, wherein said treatment is by aerosol delivery to the lower respiratory tract of said agent.

BRIEF DESCRIPTION OF THE FIGURES

FIG. 2a shows viral shedding over a 96 hour period following infection of human lung bronchial epithelial cells with influenza A virus and the effect of IFN-β treatment from 48 hours post-infection. Viral shedding plateaus between 48 and 96 hours. (n=1 experiment).

FIG. 2b shows viral shedding over a 96 hour period following infection of human lung bronchial epithelial cells with influenza A virus and the effect of IFN-β treatment from 48 hours post-infection. Viral shedding plateaus between 48 and 96 hours. (n=3 experiments including original data).

FIG. 5 shows the protective effect of human IFN-β in cynomolgus macaque cells infected with seasonal influenza (n=4). Cynomolgus macaque cells were pre-treated with IFN-β (0, 100 or 1000 IU/ml) for 24 hrs prior to infection with the flu strain A/Victoria/3/75 (H3N2) at an MOI of 0.01. Supernatants were collected 48 hrs after virus infection and viral shedding was measured by plaque assay. * indicates $p<0.05$.

FIG. 6 is a schematic illustration of the study which confirmed that IFN-β can be successfully delivered to the lung.

FIG. 7 is a schematic illustration of the study which investigates effect of prophylactic and therapeutic treatment with lung delivered IFN-β on influenza induced lung pathology and lung viral load.

BRIEF DESCRIPTION OF THE SEQUENCE LISTING

Figure 1A:
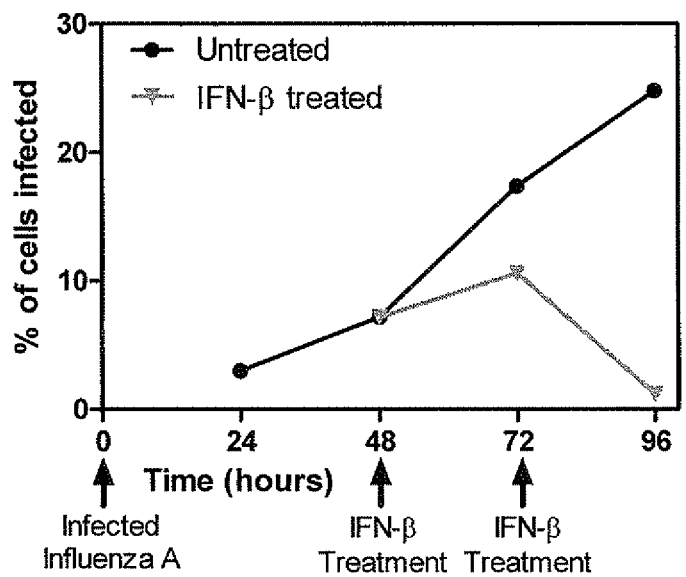
FIG. 1a shows the increase in the percentage of human lung bronchial epithelial cells infected over a 96 hour period following infection with influenza A virus and the effect of IFN-β treatment from 48 hours post-infection (n=1 experiment).

SEQ ID NO: 1 shows the nucleotide sequence of human IFN-β1a. SEQ ID NO: 2 shows the amino acid sequence of human IFN-β1a. SEQ ID NO: 3 shows the nucleotide sequence of human IFN-β1b. SEQ ID NO: 4 shows the amino acid sequence of human IFN-β1b. IFN-β1b is identical to human IFN-β1a except for replacement of the cysteine at residue 17 with serine.

DETAILED DESCRIPTION OF THE INVENTION

As hereinbefore indicated, the present invention relates to new therapeutic uses for IFN-β. In particular, it relates, for example, to therapeutic use of IFN-β by aerosol delivery to the lower respiratory tract for the treatment of individuals diagnosed as having lower respiratory tract illness that has developed during or following an influenza like illness, particularly those patients who have been admitted to hospital.

As noted above, interferons have been proposed previously for the prophylaxis or early stage treatment of ILI. Accordingly, interferons have been proposed for use either before symptoms of ILI are manifested or on the initial occurrence of such symptoms. In general, these interferons have been administered to the upper respiratory tract, eg the nasal pharynx. Usually initiation of treatment with interferons begins within 24 hours of the occurrence of symptoms.

In contrast we have found that patients who have been hospitalized with complications arising from ILI, in particular with lower respiratory tract illness may be treated by the aerosolized delivery of an interferon-β agent to the lower respiratory tract. Usually hospitalization occurs typically 48 hours after the first occurrence of symptoms.

Definition of IFN-β.

The term IFN-β as used herein will be understood to refer to any form or analog of IFN-β that retains the biological activity of native IFN-β and preferably retains the activity of IFN-β that is present in the lung and, in particular, the bronchial and/or alveolar epithelium. The IFN-β may be identical to or comprise the sequence of human IFN-β1a (SEQ ID NO: 2) or human IFN-β1b (SEQ ID NO: 4). IFN-β also refers to a variant polypeptide having an amino acid sequence which varies from that of SEQ ID NO: 2 or 4. Alternatively, IFN-β may be chemically-modified. A variant of IFN-β may be a naturally occurring variant, for example a variant which is expressed by a non-human species. Also, variants of IFN-β include sequences which vary from SEQ ID NO: 2 or 4 but are not necessarily naturally occurring. Over the entire length of the amino acid sequence of SEQ ID NO: 2 or 4, a variant will preferably be at least 80% homologous to that sequence based on amino acid identity. More preferably, the polypeptide is at least 85% or 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 40 or more, for example 60, 80, 100, 120, 140 or 160 or more, contiguous amino acids ("hard homology"). Homology may be determined using any method known in the art. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nhn.nih.gov/). This algorithm involves first identifying high scoring sequence pan: (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. ScL USA 89: 10915-10919) alignments (B) of 50, expectation (E) of 10, M=5, N=4, and a comparison of both strands. The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P (N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Amino acid substitutions may be made to the amino acid sequence of SEQ ID NO: 1 or 2, for example from 1, 2, 3, 4 or 5 to 10, 20 or 30 substitutions. Conservative substitutions may be made, for example, according to Table 1. Amino acids in the same block in the second column and preferably in the same line in the third column may be substituted for each other: Table 1—Conservative amino acid substitutions NON-AROMATIC Non-polar G A P I L V Polar—uncharged C S T M N Q Polar—charged D E H KR AROMATIC H F W Y

TABLE 1

| Conservative amino acid substitutions | | |
|---|---|---|
| NON-AROMATIC | Non-polar | G A P |
| | | I L V |
| | Polar—uncharged | C S T M |
| | | N Q |
| | Polar—charged | D E |
| | | H K R |
| AROMATIC | | H F W Y |

One or more amino acid residues of the amino acid sequence of SEQ ID NO: 1 or 2 may alternatively or additionally be deleted. From 1, 2, 3, 4 or 5 to 10, 20 or 30 residues may be deleted, or more. IFN-β also includes fragments of the above-mentioned sequences. Such fragments retain IFN-β activity. Fragments may be at least from 120 or 140 amino acids in length. Such fragments may be used to produce chimeric agents as described in more detail below. IFN-β includes chimeric proteins comprising fragments or portions of SEQ ID NO: 2 or 4. One or more amino acids may be alternatively or additionally added to the polypeptides described above. An extension may be provided at the N-terminus or C-terminus of the amino acid sequence of SEQ ID NO: 2 or 4 or polypeptide variant or fragment thereof. The extension may be quite short, for example from 1 to 10 amino acids in length. Alternatively, the extension may be longer. A carrier protein may be fused to an amino acid sequence described above. A fusion protein incorporating one of the polypeptides described above can thus be used in the invention. IFN-β also includes SEQ ID NO: 2 or 4 or variants thereof that have been chemically-modified. A number of side chain modifications are known in the art and may be made to the side chains of the proteins or peptides discussed above. Such modifications include, for example, glycosylation, phosphorylation, modifications of amino acids by reductive alkylation by reaction with an aldehyde followed by reduction with NaBH$_4$, amidination with methylacetimidate or acylation with acetic anhydride. The modification is preferably glycosylation. The IFN-β may be made synthetically or by recombinant means using methods known in the art. The amino acid sequence of proteins and polypeptides may be modified to include non-naturally occurring amino acids or to increase the stability of the compound. When the proteins or peptides are produced by synthetic means, such amino acids may be introduced during production. The proteins or peptides may also be modified following either synthetic or recombinant production. The IFN-β may also be produced using D-amino acids. In such cases the amino acids will be linked in reverse sequence in the C to N orientation. This is conventional in the art for producing such proteins or peptides. The IFN-β may be produced in a cell by in situ expression of the polypeptide from a recombinant expression vector. The expression vector optionally carries an inducible promoter to control the expression of the polypeptide. The IFN-β or analog thereof may be produced in large scale following purification by any protein liquid chromatography system after recombinant expression. Preferred protein liquid chromatography systems include FPLC, AKTA systems, the BioCad system, the Bio-RadBioLogic system and the Gilson HPLC system. Commercially available forms of IFN-β or analogs thereof may be used in the invention. Examples include Betaseron® and Avonex®.

Agents that increase IFN-β expression

The invention may also involve using an agent that increases endogenous expression of IFN-β in the lung or preferably the bronchial and/or alveolar epithelium. The agents may act directly on the promoter or other regulatory sequences of the IFN-β gene. Such agents may act to reduce the constitutive silencing of the IFN-β promoter. Alternatively, the agent may stimulate cells to produce endogenous IFN-β by acting at receptors at the cell surface. Agents that increase endogenous expression of IFN-β of interest in relation to the present invention include, but are not limited to, poly(inosinic acid)-poly(cytidylic acid) (poly(IC)), ANA773, perindopril, BL-20803, Tilorone, ABMP, DRB, Atabrine, 10-carboxy-9acridone, CP-28888, Bropirimine, and Imiquimod.

The invention may also involve using a polynucleotide which is capable of expressing IFN-β or an agent that increases endogenous expression of IFN-β in lung airways. Such a polynucleotide may preferably be in the form of a vector capable of directing expression of IFN-β or an agent that induces IFN-β in the bronchial and/or alveolar epithelium. The resulting IFN-β or agent may then have a therapeutic effect ("gene therapy"). The polynucleotide may encode any of the forms of IFN-β discussed above including the variants, fragments and chimeric proteins thereof. The polynucleotide encoding IFN-β may comprise the human sequence (SEQ ID NO: 1 or 3) or a naturally occurring sequence variant, for example a variant which is expressed by a non-human species. Also, a polynucleotide encoding IFN-β includes sequences which vary from SEQ ID NO: 1 or 3 but are not necessarily naturally occurring. Over the entire length of the amino acid sequence of SEQ ID NO: 1 or 3, a variant will preferably be at least 80% homologous to that sequence based on nucleotide identity. More preferably, the polynucleotide is at least 85% or 90% and more preferably at least 95%, 97% or 99% homologous based on nucleotide identity to the nucleotide of SEQ ID NO: 1 or 3 over the entire sequence. There may be at least 80%, for example at least 85%, 90% or 95%, nucleotide identity over a stretch of 40 or more, for example 60, 80, 100, 120, 140 or 160 or more, contiguous nucleotides ("hard homology"). Homology may be determined as discussed above. The polynucleotides may comprise DNA or RNA but preferably comprise DNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art. Polynucleotides such as a DNA polynucleotide may be produced recombinantly, synthetically, or by any means available to those of skill in the art. They may also be cloned by standard techniques. The polynucleotides are typically provided in isolated and/or purified form. Polynucleotides will generally be produced using recombinant means, for example using PCR (polymerase chain reaction) cloning techniques. This will involve making a pair of primers (e.g. of about 15-30 nucleotides) to a region of the required gene which it is desired to clone, bringing the primers into contact with DNA obtained from a suitable cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Although in general the techniques mentioned herein are well known in the art, reference may be made in particular to Sambrook et al, 1989. As hereinbefore indicated, preferably the polynucleotide is used in an expression vector wherein it is operably linked to a control sequence which is capable of providing for the expression of the coding sequence in the airways of human lung. Expression vectors for use in accordance with the invention may be any type of vector conventionally employed for gene therapy. It may be a plasmid expression vector administered as naked DNA or complexed with one or more cationic amphiphiles, e.g one or more cationic lipids, e.g. in the form of DNA/liposomes. A viral vector may alternatively be employed. Vectors for expression of therapeutic proteins in the airways of human lung have previously been described. For example, Published International Application WO 01/91800 (Isis Innovation Limited) describes for such purpose expression vectors including the human ubiquitin C promoter or functional analogues thereof. The human ubiquitin C promoter has been shown to be capable of producing high level protein expression in the airways of mice over many weeks and hence has been proposed as a favoured promoter for use in airway gene therapy for a variety of respiratory diseases. Examples of expression vectors for use in directing transgene expression in airway epithelia have also been described in Chow et al. Proc. Natl. Acad. Sci. USA 1997; 94: 14695-14700. Such expression vectors can be administered via the airways, e.g into the nasal cavity or trachea.

The IFN-β, agent or polynucleotide may be administered in a medicament or pharmaceutical composition suitable for airway delivery which will typically also include a pharmaceutically acceptable excipient. Such an "excipient" generally refers to a substantially inert material that is nontoxic and does not interact with other components of the composition in a deleterious manner. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulphates, and the like; and the salts of organic acids such as acetates, propionates, malonates, benzoates, and the like. It is also preferred, although not required, that a composition or medicament comprising the therapeutic agent will contain a pharmaceutically acceptable carrier that serves as a stabilizer, particularly for peptide, protein, polynucleotide or other like agents. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. It may also be useful to employ a charged lipid and/or detergent. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® durfactant and Triton® surfactants (available from Union Carbide Chemicals anaplastics, Danbury, Conn., Tergitol® and Triton® are registered trademarks of Union Carbide Corporation, New York), polyoxyethylenesorbitans, for example, TWEEN® surfactants (available from Atlas Chemical Industries, Wilmington, Del. Tween® is a registered trademark of Uniqema Americas LLC, Delaware), polyoxyethylene ethers, for example Brij® (Brij is a registered trademark of Uniqema Americas LLC), pharmaceutically acceptable fatty acid esters, for example, lauryl sulfate and salts thereof (SDS), and like materials. A thorough discussion of pharmaceutically acceptable excipients, carriers, stabilizers and other auxiliary substances is available in Remingtons Pharmaceutical Sciences (Mack Pub. Co., N. J. 1991).

A suitable composition for airway delivery of IFN-β may, for example, be formulated as described in U.S. Pat. No 6,030,609 by dissolving lyophilised IFN-β in a pharmaceutically acceptable vehicle such as sterile distilled water or sterile physiological saline, optionally with addition of one or more carriers, stabilizers, surfactants or other agents in order to enhance effectiveness of the IFN-β active agent.

A suitable composition has a pH of from 5 to 8, more preferably 5.5 to 7.5. Preferably, the composition is buffered, e.g. using a citrate buffer.

The Rentschler composition, which is based on formulations disclosed in U.S. Pat. No. 6,030,609, has a pH of 6.5 and osmolarity of 290 mOsm/kg. The composition is preferably provided as a sterile, clear and colourless, ready-to-use aqueous nebuliser solution presented in a disposable glass syringe.

In addition to the active ingredient, the composition preferably comprises a buffering system to maintain the pH at between 5 and 8, more preferably 5.5 and 7.5, especially 6.5. The composition also preferably comprises an antioxidant, for example, DL-methionine.

A preferred composition comprises:

| Ingredients | Quantity (per mL) | Function | Monograph |
|---|---|---|---|
| Active substance | | | |
| IFN-β1a (RB) | 11.3 MIU (40 µg) | Active ingredient | HSE |
| Excipients | | | |
| Sodium dihydrogen phosphate dihydrate | 5.92 mg | Buffer component | Ph. Eur. |
| Disodium phosphate dihydrate | 2.13 mg | Buffer component | Ph. Eur. |
| Sodium citrate | 20.58 mg | Chelating agent, buffer component | Ph. Eur. |
| DL-methionine | 0.30 mg | Stabiliser, antioxidant | Ph. Eur. |
| Water for injections to | 1 mL | Solvent | Ph. Eur. |

A composition comprising a therapeutically effective amount of the IFN-β, agent or polynucleotide described herein may conveniently be delivered to the lung airways by means of an inhalation device that is capable of delivering fine particles of the active ingredient to the lower respiratory tract or airways. Typically particles of the active ingredient will have a mass median diameter of 1-10 microns. Suitable inhalation devices include dry powder inhalation (DPI) devices, pressurised metered dose inhalers (pMDI) and aerosol nebulisers.

Typically, the inhalation device will produce an aerosol with a particle size, as determined using a Malvern Masterizer S, with a mass median diameter of 1-10 micron, preferably 3-8 micron, in which mass per cent have a diameter below 5 micron is from 25-80%, preferably 30-65%. A suitable nebulizier is the I-neb device, a CE-marked nebuliser manufactured by Philips Respironics.

An appropriate effective amount may be determined by appropriate clinical testing and will vary with for example the activity of the IFN-β administered or induced. The IFN-β, agent or polynucleotide may for example, be administered in microgram amounts.

They are administered to the subject to be treated in a manner compatible with the dosage formulation, and in an amount that will be effective to bring about the desired effect. The amount to be delivered per dose may be 0.1 µg to 500 µg, for example 1 to 50 µg, depending on the subject to be treated.

The treatment normally lasts from 5-7 days and may continue to 14 days if symptoms persist. Treatment may be given from every other day to several times a day. Preferably, treatment is given once per day.

The IFN-β, agent or polynucleotide may be administered on its own or simultaneously, sequentially or separately in combination with another therapeutic compound. In particular, the IFN-β, agent or polynucleotide may be administered in conjunction with a therapeutic compound used to treat the respiratory disease or antiviral to the individual. The IFN-β, agent or polynucleotide and additional therapeutic compound may be formulated in the same or different compositions.

In one embodiment, the IFN-β, agent or polynucleotide is administered to an individual with asthma in combination with an inhaled corticosteroid.

In a further embodiment, the IFN-β, agent or polynucleotide may be administered simultaneously, sequentially or separately with an inhaled neuraminidase inhibitor. Thus, in a further aspect of the present invention there is provided a product for treatment of individuals diagnosed as having lower respiratory tract disease (or symptoms) that have developed during or following an influenza like illness comprising for simultaneous, separate or sequential lower respiratory tract administration (i) a first agent selected from (a) IFN-β, (b) an agent that increases IFN-β expression and (c) a polynucleotide capable of expressing (a) or (b) and (ii) an inhaled neuraminidase inhibitor. Preferably, such a product will provide for simultaneous, separate or sequential administration of IFN-β and an inhaled neuraminidase inhibitor, for example, zanamivir. A first agent as defined above and an inhaled neuraminidase inhibitor may, for example, be provided in the form of a single pharmaceutical composition suitable for aerosol delivery to the airways, e.g., by means of a dry powder inhaler, a pressurised metered dose inhaler or an aerosol nebulizer.

Alternatively, the IFN-β, agent or polynucleotide may be administered simultaneously, sequentially or separately with an oral neuraminidase inhibitor, such as oseltamivir.

Alternatively, the IFN-β, agent or polynucleotide may be administered simultaneously, sequentially or separately with a systemically administered neuraminidase inhibitor, such as peramivir.

In a further embodiment, the IFN-β, agent or polynucleotide may be administered simultaneously, sequentially or separately with an inhaled influenza virus attachment inhibitor. Thus, in a further aspect of the present invention there is provided a product for treatment of individuals diagnosed as having lower respiratory tract disease (or symptoms) that have developed during or following an influenza like illness comprising for simultaneous, separate or sequential lower respiratory tract administration (i) a first agent selected from (a) IFN-β, (b) an agent that increases IFN-β expression and (c) a polynucleotide capable of expressing (a) or (b) and (ii) an inhaled influenza virus attachment inhibitor. Preferably, such a product will provide for simultaneous, separate or sequential administration of IFN-β and an influenza virus attachment inhibitor, for example, the sialidase fusion protein, DAS181 (Fludase®). A first agent as defined above and an inhaled influenza virus attachment inhibitor may, for example, be provided in the form of a single pharmaceutical composition suitable for aerosol delivery to the airways.

In a further embodiment, the IFN-β, agent or polynucleotide may be administered simultaneously, sequentially or separately with an antibacterial antibiotic. Preferably the antibacterial antibiotic is administered by inhalation.

In a further embodiment, the IFN-β, agent or polynucleotide may be administered simultaneously, sequentially or separately with an antifungal antibiotic. Preferably the antifungal antibiotic is administered by inhalation.

Children younger than 5, but especially children younger than 2 years old, adults 65 years of age and older, pregnant women and those with co-morbidities (e.g. chronic lung disease, neurological and neurodevelopmental conditions, heart disease, blood disorders, endocrine disorders, kidney disorders, liver disorders, metabolic disorders, malignancy and weakened immune system due to disease or medication) are at greatest risk of developing complications resulting in hospitalisation and have the poorest outcomes and represent a particular target group for the invention. Elderly individuals, for example those more than 60 years of age are a particular target group, as are patients suffering from asthma and/or COPD.

A further at risk group are patients who have not previously been exposed to an ILI.

EXAMPLE 1

The ability of exogenous IFN-β to suppress influenza A infection in an in vitro model of established infection of the lower respiratory tract is illustrated in the following example.

Overview

Lower respiratory tract disease (or symptoms) that develop during or following an influenza-like illness (ILI) are often precipitated by the spread of virus infections from the upper to the lower respiratory tract. Furthermore, prolonged symptoms and, in hospitalised patients, extended hospital stays are associated with persistent viral shedding in the lower airways. Using human lung bronchial epithelial cells, an important site of influenza replication in man, we have developed a model of established influenza A infection of the lower respiratory tract. The effect of IFN-β in this model was investigated.

Method

Cell Culture and Infection Protocol

Human lung bronchial epithelial (HBE) cells were cultured in minimum essential medium (MEM) containing glutamax (Invitrogen), 10% fetal bovine serum (FBS) (Invitrogen), penicillin (50 U/ml) and streptomycin (50 µg/ml) (Invitrogen). HBE cells were plated at $1.5 \times 10^5$/well, passage 41-49, in a 24 well plate. At approximately 60-70% confluency, the cells were cultured in reduced serum medium (MEM containing glutamax (Invitrogen) and 0.75-1% FBS (Invitrogen)) for 24 hours. Cells were infected with an activated influenza strain (influenza A/WSN/33 (H1N1) (Retroscreen)) at 0.0001 MOI at 37° C. After one hour, unbound virus was removed by washing. Reduced serum medium was added and the cells were incubated at 37° C. for a further four days. Cells were treated with 10001 U/ml of human IFN-β1a (Rentschler) 48 hrs post-infection with virus. Once IFN-β treatment commenced the dose was repeated every 24 hrs.

Flow Cytometry to Determine Percentage Influenza Positive Cells

Cell media was collected at 24, 48, 72, and 96 hours post-infection and stored at −80° C. At 24, 48, 72 and 96 hours post-infection cells were trypsinised, counted and washed in phosphate buffered saline (PBS). Up to $2 \times 10^5$ cells were taken for analysis by flow cytometry. The cells were centrifuged at 400 g and the supernatant discarded. Live/dead cell stain (Molecular Probes) was reconstituted in dimethyl sulfoxide (DMSO) (500 µl) and diluted 1:100 in PBS. Diluted live/dead cell stain (100 µl) was incubated with cells at room temperature for 30 minutes. Cells were washed in PBS, centrifuged at 400 g, and the supernatant discarded. 250 µl Cytofix/Cytoperm (BD Biosciences) was added per tube and the cells left at 4° C. for 20 minutes. Cells were washed twice with 2 ml Perm/Wash (BD Biosciences) solution by centrifugation at 500 g. After the second wash, cells were re-suspended in 100 µl Perm/Wash solution and left at room temperature for 15 minutes. Anti-influenza A matrix protein antibody (Serotec) was diluted to 2.5 µg/ml in Perm/Wash solution and 100 µl added to cells for 30 minutes at room temperature. Cells were washed twice with 2 ml Perm/Wash solution by centrifugation at 500 g. Anti-mouse IgG-FITC (Sigma) was diluted to 5 µg/ml in Perm/Wash solution and 100 µl added to cells for 30 minutes at room temperature protected from light. Cells were washed twice with 2 ml Perm/Wash solution by centrifugation at 500 g. Cells were resuspended in Perm/Wash solution and analysed by flow cytometry using the FACSCalibur (BD Biosciences) and CellQuest Pro software. Data was subsequently analysed using WinMDI software.

Plaque Assay to Determine Viral Shedding

Madin Darby canine kidney (MDCK) cells were cultured in MEM containing glutamax (Invitrogen), 10% FBS (Invitrogen), non-essential amino acids (Invitrogen), and penicillin/streptomycin (Invitrogen). MDCK cells were plated at $1 \times 10^5$ cells/well, passage 25-30, in a 12 well plate. On reaching 100% confluence cells were washed twice with PBS. Cell media collected during the infection experiment was diluted in serum-free media (DMEM (Invitrogen), penicillin/streptomycin (Invitrogen), L-glutamine (Invitrogen), Non-essential amino acids (Invitrogen), and sodium pyruvate (Invitrogen)) to give a dilution range of ten-fold dilutions between 1:10 to $1:10^6$. Diluted cell media (200 µl) was added to duplicate wells. Plates were incubated at 37° C. for 1 hr. Virus was aspirated and cells washed with PBS. Overlay medium (100 ml 10 times concentrated MEM (Invitrogen), 20 ml 7.5% sodium bicarbonate (Sigma), 10 ml 1M HEPES (Fluka), 28 ml 7.5% bovine serum albumin (BSA) fraction V (Sigma), 5 ml 1% DEAE-dextran (Sigma), 20 ml penicillin/streptomycin (Invitrogen), 10 ml 200 mM glutamine (Invitrogen), 507 ml d.H$_2$O) was prepared and 17.5 ml added to 12.5 µl 1 mg/ml trypsin treated with L-(tosylamido-2-phenyl) ethyl chloromethyl ketone (TRTPCK trypsin) (Worthington Biochemical Corp.) and 7.5 ml Avicel suspension (4.8 g Avicel (FMC Biopolymer) in 186 ml d.H$_2$O). The overlay was mixed by inverting and 1 ml added per well. Plates were incubated for 2 days without moving or shaking. Overlay medium was aspirated and cells washed twice with PBS. Crystal violet solution was added (0.5 ml) (0.65 g crystal violet (Sigma), 25 ml formaldehyde (Sigma), 25 ml 100% ethanol (Sigma), 450 ml 1×PBS (5 DuIA PBS tablets (Sigma) +500 ml d.H$_2$O)) for 30 minutes at room temperature. Crystal violet was removed and plates washed in water. Plates were allowed to dry and plaques counted.

Three independent experiments were conducted. Data from the first experiment and summary data are presented.

Data Analysis

Data was Analysed Using Graphpad Prism Software

Results

Figure 1B:
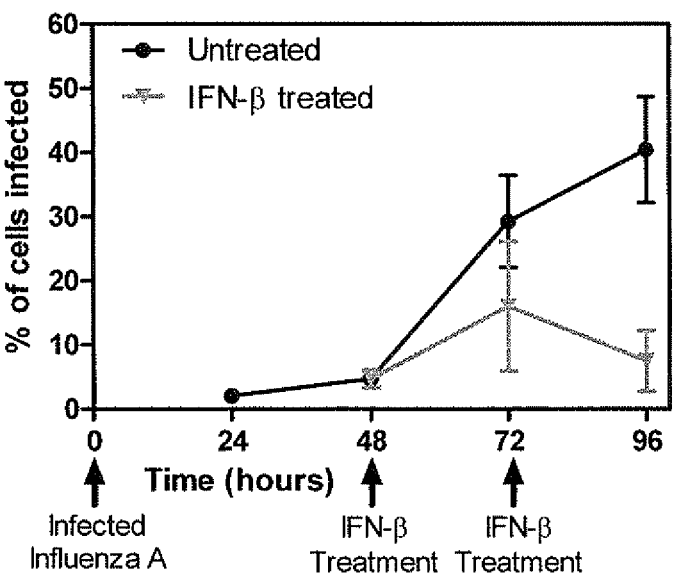
FIG. 1b shows the increase in the percentage of human lung bronchial epithelial cells infected over a 96 hour period following infection with influenza A virus and the effect of IFN-β treatment from 48 hours post-infection (n=3 experiments including original data).

In this model flow cytometric analysis suggests that between 5 and 40% of cells are infected between 48 and 96 hours (Refer to FIGS. 1a and 1b) which is similar to the levels of productively infected cells reported in the clinical setting at peak infection (Baccam et al. (2006) Journal of Virology, 80: 7590-7599). Correspondingly this period is also associated with highest levels of virus shedding in our model (FIGS. 2a and 2b).

Treatment of cells with IFN-β at 48 hours post-infection, modelling treatment of established infection, caused a large reduction in the proportion of infected cells and viral shedding (FIGS. 1a, 1b, 2a and 2b). A reduction in viral load of greater than 10 fold is considered to be clinically relevant (Barnett et al. (2000) Antimicrob. Agents Chemother 44: 78-87).

Conclusion

These results show that IFN-β treatment has the potential to alter the course of established influenza infection in the lungs and thus to reduce respiratory tract illness that develops during or following an established influenza-like illness (ILI). As elderly patients and those suffering from asthma and/or COPD are likely to have difficulty in making IFN-β when needed, the uses and methods described herein are of particular application to such vulnerable groups.

In vivo Study:

Introduction

The main complication of influenza—like illness is viral pneumonia that develops following the spread of the virus to the lower respiratory tract.

Figure 3:
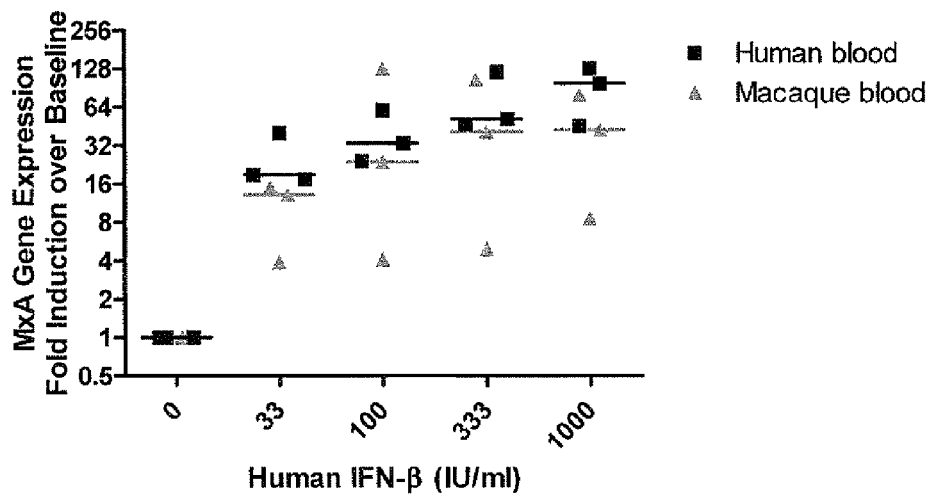
FIG. 3 shows the effect of human IFN-β treatment on the expression of the IFN-β-dependent antiviral gene myxovirus resistance protein 1 (MxA) (n=3) in blood cells from healthy human volunteers or cynomolgus macaques. Whole blood was treated with IFN-β (0-1000 IU/ml) for 4 hours, RNA extracted and effect on MxA gene expression measured.
Figure 4:
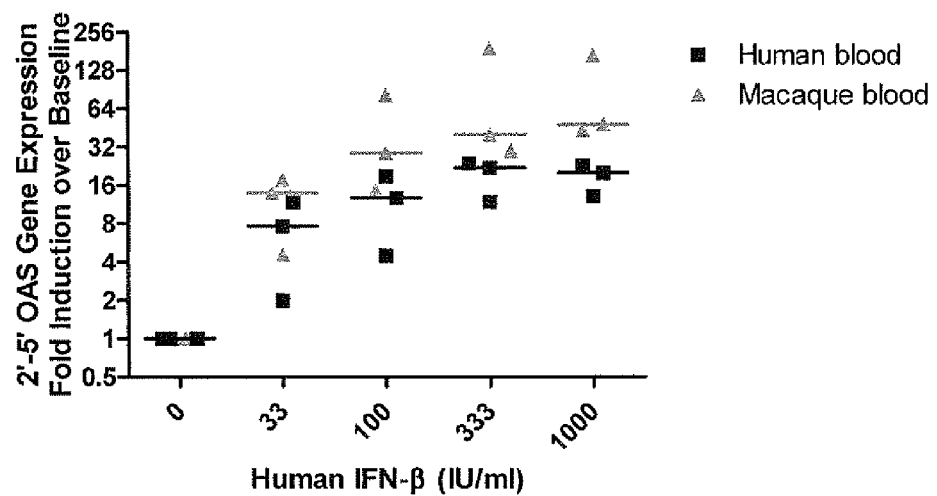
FIG. 4 shows the effect of human IFN-β treatment on the expression of the IFN-β-dependent antiviral gene 2'-5' oligoadenylate synthetase (2'-5' OAS) (n=3) in blood cells from healthy human volunteers or cynomolgus macaques. Whole blood was treated with IFN-β (0-1000 IU/ml) for 4 hours, RNA extracted and effect on 2'-5' OAS gene expression measured.

Human IFN-β is highly species specific in its biological activity. The cynomolgus macaque monkey is an appropriate species to study the effects of human IFN-β. Human IFN-β has been shown to upregulate the interferon-sensitive antiviral genes myxovirus resistance protein 1 (MxA) (FIGS. 3) and 2'-5' oligoadenylate synthetase (2'-5' OAS) (FIG. 4) to the same extent in cynomolgus macaque blood cells and human blood cells. Furthermore in in vitro studies human IFN-β protects cynomolgus macaque cells from infection with influenza (FIG. 5).

Preclinical models of lower respiratory tract illness have been developed using the cynomolgus macaque monkey for highly pathogenic influenza A (H5N1) (Rimmelzwaan et al. (2001) J Virol. 75: 6687-91) and pandemic 2009 influenza A (H1N1) (Herfst et al. (2010) Vet. Pathol. 47: 1040-7) viruses. These models have predicted the clinical efficacy of neuraminidase inhibitors against influenza when administered prior to infection.

This study investigates the effect of lung delivered IFN-β in a similar cynomolgus macaque monkey model of influenza induced lower respiratory tract illness. The challenge virus strains are A/Indonesia/5/05 (H5N1) and A/Netherlands/602/2009 (pandemic H1N1) which have both been shown to replicate in the lower respiratory tract and cause significant lung pathology (Herfst et al. (2010) Vet. Pathol. 47: 1040-7; Rimmelzwaan et al. (2001) J Virol. 75: 6687-91).

The study comprises two stages. In the first stage successful delivery of inhaled IFN-β is established by showing upregulation of IFN-β-dependent antiviral markers in lung cells obtained by broncho-alveolar lavage (BAL). Similar data in clinical studies have supported further development of inhaled IFN-β as an antiviral therapy. In the second stage the effect of prophylactic and therapeutic treatment with lung delivered IFN-β on influenza induced lung pathology and lung viral load is investigated.

Stage 1: Confirmation of Successful Delivery of IFN-β to the Lung

In brief, IFN-β, in solution, is administered by nebuliser on two occasions to the lungs of cynomolgus macaque monkeys. BAL is collected prior to and following each dose. Gene expression of IFN-β-dependent antiviral markers (MxA, 2'-5' OAS and Interferon gamma-induced protein 10 kDa (IP-10) in BAL cells is determined using quantitative PCR methods.

Levels of upregulation are compared to the data generated in clinical studies in order to select the dose for the next stage. The study schedule and more details of the methods are described below.

Seven days prior to administration of inhaled IFN-β, five male cynomolgus macaques, aged approximately three years, are anaesthetized with ketamine-dormitor, have blood and broncho-alveolar lavage (BAL) collected and their weight measured. BAL involves flushing the lungs with 10 mL phosphate-buffered saline with an envisaged recovery of approximately 5 mL. On each occasion BAL samples are separated into supernatant and cellular fraction. The cellular fractions are lysed in RLT buffer (Qiagen) and analysed for the IFN-β-dependent antiviral biomarkers MxA, 2'-5' OAS, and IP-10 using quantitative PCR methods.

On day 0, under anaesthesia, blood is collected, weight measured and 3 ml inhaled IFN-β (Rentschler) delivered to each macaque. IFN-β nebuliser solution is delivered by inhalation using the I-neb device (Philips Respironics) coupled to a pediatric face mask (Philips Respironics, part number HS81110EU-001). The I-neb device is programmed to generate a continuous stream of aerosol when switched on.

On day 1, under anaesthesia, blood and BAL are collected and weight measured.

On day 8, under anaesthesia, blood is collected, weight measured and 1.5 ml or 4.5 ml inhaled IFN-β delivered to each macaque. The dose of IFN-β selected will be dependent on the results obtained from dose 1.

On day 9, under anaesthesia, blood and BAL is collected and weight measured.

Stage 2: Effect of Prophylactic and Therapeutic Treatment with Lung Delivered IFN-β on Influenza Induced Lung Pathology and Lung Viral Load The second stage of the study includes three treatment groups: Group1 receives placebo; Group 2 receives inhaled IFN-β treatment 24 hrs prior to being infected with challenge virus and subsequent daily treatment with IFN-β; Group 3 receives inhaled IFN-β treatment 4 hours after being infected with challenge virus and subsequent daily treatment with IFN-β. Therapeutic treatments are administered 4 hours post infection as in this model a relatively high dose of virus is administered directly to the lower respiratory tract to model established lower airways disease. A sample size calculation indicated that 9 animals per group is required to see a treatment effect of a 1.5 log difference in viral titre between treated and control (untreated) animals. This is considered to be clinically significant on the basis of results of clinical studies with the neuraminidase inhibitors (Barnett et al. (2000) Antimicrob. Agents Chemother. 44: 78-87). The study schedule is shown below:

Due to the number of animals included in the study a block design is used. The study is conducted in three blocks, with each block consisting of nine animals, three animals from each treatment group.

Fourteen days prior to virus challenge nine cynomolgus macaques confirmed as seronegative for circulating influenza viruses are equipped with a pre-programmed temperature sensor in the abdominal cavity and blood is collected under ketamine and dormitor anaesthesia.

On day −1, after full recovery from surgery, all animals are anaesthetised, weighed and samples (whole blood for serum and nasal/throat swabs) collected. Animals belonging to Groups 1 and 2 are administered nebulised placebo or IFN-β (at the dose determined in stage 1) under anaesthesia.

On day 0 animals of Group 1 and 2 are treated with nebulised placebo or IFN-β as described above. All animals are then challenged intratracheally with influenza virus ($10^5$ $TCID_{50}$ H5N1 or $10^7$ $TCID_{50}$ H1N1). Four hours after intratracheal challenge animals of Group 3 are administered nebulised IFN-β as described above.

On days 1, 2, 3, and 4 all animals are anaesthetised, weighed, samples collected (whole blood for serum and nasal/throat swabs) and treated with nebulised placebo or IFN-β as described above.

Five days after challenge all animals are anaesthetised, weighed and euthanized by exsanguinations. Full gross pathology is performed, all major organs inspected and lung lesions described. Samples are collected from all animals including: whole blood for serum, nasal/throat swabs and tissue from the right lung. Swabs collected throughout the experiment and sections of the right lung are subjected to quantitative PCR and virus titration to determine viral load. The left lung is inflated with 10% formalin for subsequent histopathological assessment.

The main endpoints are lung viral load and lung pathology score. Throat swabs taken daily will give an indication of the time course of the viral infection. Positive data, a reduction in lung viral load or lung pathology, particularly following therapeutic treatment with IFN-β, would support the development of inhaled IFN-β for the treatment of lower respiratory tract illness caused by influenza.

The invention claimed is:

1. A method of treating an individual diagnosed with a lower respiratory tract illness that has developed during or following an established influenza like illness (ILI) caused by influenza virus, wherein established ILI means an illness in which the symptoms have been apparent for at least 48 hours and wherein ILI is defined as a fever >37.8° C. plus:

1) two of the following symptoms: headache, cough, sore throat and myalgia; and/or 2) confirmed influenza; said method comprising aerosol administration of interferon-β (IFN-β) to the lower respiratory tract of the individual, and wherein said method results in a beneficial effect on the course of said illness.

2. The method according to claim 1, wherein the IFN-β comprises the sequence of:

(a) human IFN-β (SEQ ID NO: 2); or (b) human IFN-β1b (SEQ ID NO: 4).

3. The method according to claim 1, wherein said agent is combined with a neuraminidase inhibitor for simultaneous, separate or sequential administration.

4. The method according to claim 1, wherein the individual is suffering from asthma and/or COPD.

5. The method according to claim 1, wherein the individual is more than 60 years of age.

* * * * *

SEQUENCE LISTING

```
<160> NUMBER OF SEQ ID NOS: 4

<210> SEQ ID NO 1
<211> LENGTH: 757
<212> TYPE: DNA
<213> ORGANISM: Homo sapiens
<220> FEATURE:
<221> NAME/KEY: CDS
<222> LOCATION: (64)..(564)

<400> SEQUENCE: 1
atgaccaaca agtgtctcct ccaaattgct ctcctgttgt gcttctccac tacagctctt      60 tcc atg agc tac aac ttg ctt gga ttc cta caa aga agc agc aat ttt      108
    Met Ser Tyr Asn Leu Leu Gly Phe Leu Gln Arg Ser Ser Asn Phe
    1               5                   10                  15 cag tgt cag aag ctc ctg tgg caa ttg aat ggg agg ctt gaa tat tgc      156
Gln Cys Gln Lys Leu Leu Trp Gln Leu Asn Gly Arg Leu Glu Tyr Cys
```

```
                     20                    25                   30 ctc aag gac agg atg aac ttt gac atc cct gag gag att aag cag ctg    204
Leu Lys Asp Arg Met Asn Phe Asp Ile Pro Glu Glu Ile Lys Gln Leu
         35                   40                  45 cag cag ttc cag aag gag gac gcc gca ttg acc atc tat gag atg ctc    252
Gln Gln Phe Gln Lys Glu Asp Ala Ala Leu Thr Ile Tyr Glu Met Leu
     50                   55                  60 cag aac atc ttt gct att ttc aga caa gat tca tct agc act ggc tgg    300
Gln Asn Ile Phe Ala Ile Phe Arg Gln Asp Ser Ser Ser Thr Gly Trp
 65                   70                  75 aat gag act att gtt gag aac ctc ctg gct aat gtc tat cat cag ata    348
Asn Glu Thr Ile Val Glu Asn Leu Leu Ala Asn Val Tyr His Gln Ile
 80                   85                  90                  95 aac cat ctg aag aca gtc ctg gaa gaa aaa ctg gag aaa gaa gat ttt    396
Asn His Leu Lys Thr Val Leu Glu Glu Lys Leu Glu Lys Glu Asp Phe
                 100                  105                 110 acc agg gga aaa ctc atg agc agt ctg cac ctg aaa aga tat tat ggg    444
Thr Arg Gly Lys Leu Met Ser Ser Leu His Leu Lys Arg Tyr Tyr Gly
             115                  120                 125 agg att ctg cat tac ctg aag gcc aag gag tac agt cac tgt gcc tgg    492
Arg Ile Leu His Tyr Leu Lys Ala Lys Glu Tyr Ser His Cys Ala Trp
         130                  135                 140 acc ata gtc aga gtg gaa atc cta agg aac ttt tac ttc att aac aga    540
Thr Ile Val Arg Val Glu Ile Leu Arg Asn Phe Tyr Phe Ile Asn Arg
 145                  150                  155 ctt aca ggt tac ctc cga aac tga agatctccta gcctgtccct ctgggactgg    594
Leu Thr Gly Tyr Leu Arg Asn
 160                  165 acaattgctt caagcattct tcaaccagca gatgctgttt aagtgactga tggctaatgt    654
actgcaaatg aaaggacact agaagatttt gaaatttta ttaaattatg agttattttt    714
atttatttaa attttatttt ggaaaataaa ttattttggg tgc                    757

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
 1               5                   10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
             100                 105                 110

Arg Gly Lys Leu Met Ser Ser Leu His Leu Lys Arg Tyr Tyr Gly Arg
         115                 120                 125

Ile Leu His Tyr Leu Lys Ala Lys Glu Tyr Ser His Cys Ala Trp Thr
     130                 135                 140
```

```
Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 3
<211> LENGTH: 720
<212> TYPE: DNA
<213> ORGANISM: Homo sapiens
<220> FEATURE:
<221> NAME/KEY: CDS
<222> LOCATION: (64)..(564)

<400> SEQUENCE: 3

```
atgaccaaca agtgtctcct ccaaattgct ctcctgttgt gcttctccac tacagctctt    60 tcc atg agc tac aac ttg ctt gga ttc cta caa aga agc agc aat ttt    108
    Met Ser Tyr Asn Leu Leu Gly Phe Leu Gln Arg Ser Ser Asn Phe
    1               5                   10                  15 cag agt cag aag ctc ctg tgg caa ttg aat ggg agg ctt gaa tat tgc    156
Gln Ser Gln Lys Leu Leu Trp Gln Leu Asn Gly Arg Leu Glu Tyr Cys
                20                  25                  30 ctc aag gac agg atg aac ttt gac atc cct gag gag att aag cag ctg    204
Leu Lys Asp Arg Met Asn Phe Asp Ile Pro Glu Glu Ile Lys Gln Leu
            35                  40                  45 cag cag ttc cag aag gag gac gcc gca ttg acc atc tat gag atg ctc    252
Gln Gln Phe Gln Lys Glu Asp Ala Ala Leu Thr Ile Tyr Glu Met Leu
        50                  55                  60 cag aac atc ttt gct att ttc aga caa gat tca tct agc act ggc tgg    300
Gln Asn Ile Phe Ala Ile Phe Arg Gln Asp Ser Ser Ser Thr Gly Trp
    65                  70                  75 aat gag act att gtt gag aac ctc ctg gct aat gtc tat cat cag ata    348
Asn Glu Thr Ile Val Glu Asn Leu Leu Ala Asn Val Tyr His Gln Ile
80                  85                  90                  95 aac cat ctg aag aca gtc ctg gaa gaa aaa ctg gag aaa gaa gat ttt    396
Asn His Leu Lys Thr Val Leu Glu Glu Lys Leu Glu Lys Glu Asp Phe
                100                 105                 110 acc agg gga aaa ctc atg agc agt ctg cac ctg aaa aga tat tat ggg    444
Thr Arg Gly Lys Leu Met Ser Ser Leu His Leu Lys Arg Tyr Tyr Gly
            115                 120                 125 agg att ctg cat tac ctg aag gcc aag gag tac agt cac tgt gcc tgg    492
Arg Ile Leu His Tyr Leu Lys Ala Lys Glu Tyr Ser His Cys Ala Trp
        130                 135                 140 acc ata gtc aga gtg gaa atc cta agg aac ttt tac ttc att aac aga    540
Thr Ile Val Arg Val Glu Ile Leu Arg Asn Phe Tyr Phe Ile Asn Arg
    145                 150                 155 ctt aca ggt tac ctc cga aac tga agatctccta gcctgtccct ctgggactgg    594
Leu Thr Gly Tyr Leu Arg Asn
160             165 acaattgctt caagcattct tcaaccagca gatgctgttt aagtgactga tggctaatgt    654
actgcaaatg aaaggacact agaagatttt gaaattttta ttaaattatg agttattttt    714
atttat                                                               720
```

<210> SEQ ID NO 4
<211> LENGTH: 166
<212> TYPE: PRT
<213> ORGANISM: Homo sapiens

<400> SEQUENCE: 4

```
Met Ser Tyr Asn Leu Leu Gly Phe Leu Gln Arg Ser Ser Asn Phe Gln
1               5                   10                  15
```

-continued

```
Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```